United States Patent [19]
Carrel et al.

[11] Patent Number: 5,882,659
[45] Date of Patent: Mar. 16, 1999

[54] USE OF A POLYHOLOSIDE IN A CLEANING OR MAKE-UP-REMOVING COMPOSITION AND COMPOSITION COMPRISING SAME

[75] Inventors: Marie-Laure Carrel, Paris; Lien Bui-Bertrand, Savigny Sur Orge, both of France

[73] Assignee: L'Oreal, Paris, France

[21] Appl. No.: 759,132

[22] Filed: Dec. 2, 1996

[30] Foreign Application Priority Data

Dec. 1, 1995 [FR] France .................................. 95 14470
May 21, 1996 [FR] France .................................. 96 06288

[51] Int. Cl.$^6$ ................................ A61K 7/02; A61K 7/48
[52] U.S. Cl. ........................ 424/401; 424/78.03; 514/844; 514/846; 514/944
[58] Field of Search ..................... 424/430, 401, 424/70.13, 78.03; 514/54, 844, 846, 944

[56] References Cited

U.S. PATENT DOCUMENTS 3,939,260  2/1976  Lafon .
5,518,733  5/1996  Lamoothe et al. .
5,703,041  12/1997 Afriat et al. ................................ 514/2

FOREIGN PATENT DOCUMENTS 0 285 829  10/1988  European Pat. Off. .
0 569 591  11/1993  European Pat. Off. .
2 068 447  8/1991   France .
WO 92/06778  4/1992  WIPO .
WO 93/00067  7/1993  WIPO .

*Primary Examiner*—Robert H. Harrison
*Attorney, Agent, or Firm*—Finnegan, Henderson, Farabow, Garrett & Dunner, L.L.P.

[57] ABSTRACT

The invention relates to the use of a polyholoside in a composition to clean and/or remove make-up from the skin, the mucous membranes, or the eyes. This composition may also comprise a cosmetically or dermatologically acceptable support.

26 Claims, No Drawings

USE OF A POLYHOLOSIDE IN A CLEANING OR MAKE-UP-REMOVING COMPOSITION AND COMPOSITION COMPRISING SAME

The present invention relates to the use of a polyholoside in a composition, particularly a cosmetic composition intended to clean and/or remove make-up from the skin, the mucous membranes, or the eyes.

It is known to use make-up-removing oils in compositions for removing make-up from the skin and/or the eyes. Generally, these compositions also comprise surfactants which allow the removal of the oil and/or of traces of make-up to be improved. However, it is known that the use of these compositions may leave an impression of discomfort, in particular on the eyelids and/or on the eyes.

Make-up-removing compositions based only on surfactants are also known. These compositions allow the removal of traces of make-up and at the same time facilitate their emulsification, thereby making the fatty and aqueous phases of the composition compatible when it is in the form of an emulsion. However, surfactants can have the drawback of being relatively irritating to the skin.

The aim of the present invention is to overcome the drawbacks of the prior art and to provide a composition which allows simple and adequate cleaning and/or removal of make-up, which is not irritating to the skin and/or the eyes and which contains substantially no surfactant, i.e., minor amounts of at least one surfactant may be present, but such amounts are neither substantially irritating to the skin nor effective for removing make-up.

A subject of the present invention is thus the use of at least one heterogeneous polyholoside in a composition to clean and/or remove make-up from the skin and/or the mucous membranes and/or the eyes, this composition comprising a cosmetically or dermatologically acceptable support, in which the heterogeneous polyholoside comprises at least one fucose unit and/or the heterogeneous polyholoside is substituted with at least one fatty chain preferably having 8–30 carbon atoms and/or the polyholoside is an alginate.

Another subject of the invention is a composition to clean and/or remove make-up from the skin andlor the mucous membranes and/or the eyes, this composition comprising at least one heterogeneous polyholoside selected from heterogeneous polyholosides comprising at least one fucose unit, polyholosides of alginate type, and heterogeneous polyholosides substituted with at least one fatty chain preferably having 8–30 carbon atoms.

Yet another subject of the invention is a process for cleaning and/or removing make-up from the skin and/or the mucous membranes and/or the eyes, wherein a cosmetically effective amount of a composition as defined above is applied to the skin and/or to the mucous membranes and/or to the eyes.

It has indeed been observed that the use of a polyholoside according to the invention makes it possible to obtain a cleaning andlor make-up-removing composition which is non-irritating or only slightly irritating and only slightly sticky, and which furthermore has a soft and pleasant feel.

Another advantage afforded by the use of such a polyholoside is the improvement in the stabilization of the final composition, when it is in emulsion form, by virtue of the self-emulsifying properties of the polyholoside employed, in particular when the polyholoside employed is a heterogeneous polyholoside which comprises at least one fucose unit.

Furthermore, the incorporation of a polyholoside into compositions, in particular cosmetic compositions, allows a gelled composition to be obtained without the addition of a conventionally-used gelling agent. The gel obtained is smooth and creamy.

A subject of the present invention is thus the use of at least one heterogeneous polyholoside as a make-up-removing agent and/or in a make-up-removing composition.

Saccharides, of formula $C_n(H_2O)_n$, are generally divided into two categories: oses or simple sugars, and osides or combination of several molecules.

Among the osides, a distinction may be made between (1) holosides which are formed solely from sugars and (2) heterosides which contain one or more oses and a non-glucidic part.

Furthermore, among the polyholosides, a distinction may also be made between homogeneous polyholosides which result from the combination of one and the same ose, and heterogeneous polyholosides which result either from the combination of different oses or from the combination of oses having the same chemical empirical formula but different geometrical configurations (D and L isomers for example), which are also considered in the present description as different oses.

It is this final category, containing the heterogeneous polyholosides, which the present invention more particularly concerns.

Thus, the heterogeneous polyholoside according to the invention contains solely sugars and results from the combination of at least two different oses.

The polyholosides according to the invention may consist of 2 to 10 oses, these compounds commonly being referred to as oligoholosides, or more than 10 oses, these compounds commonly being referred to as polyholosides.

The oses present in the polyholoside according to the invention may be selected from all the oses which may be envisaged, of natural or synthetic origin, and in particular those such as:

aldoses, for instance,
- pentoses: ribose, arabinose, xylose and apiose, for example,
- hexoses: glucose, fucose, mannose and galactose, for example, ketoses such as fructose, deoxyoses, such as rhamnose, digitoxose, cymarose and oleandrose, ose derivatives such as uronic acids, for instance mannuronic acid, guluronic acid, galacturonic acid and glycuronic acid, or alternatively itols, for instance mannitol and sorbitol.

Within the context of the present invention, a heterogeneous polyholoside may be used alone or as a mixture of heterogeneous polyholosides.

The polyholoside according to the invention may be branched or linear. It may also be substituted, for example with at least one fatty chain comprising, in particular, 8 to 30 carbon atoms.

Moreover, the polyholoside according to the invention may be an alginate (poly mannuronate and guluronate) such as a sodium alginate, a propylene glycol alginate, a calcium alginate or a glyceryl alginate.

However, the heterogeneous polyholoside preferably comprises at least one fucose unit, which may be present in an amount of from 10 to 90% by weight, preferably from 15 to 35% by weight, relative to the total weight of polyholoside solids.

In particular, the polyholoside according to the invention may comprise fucose, galactose and galacturonic acid units and, for example, may comprise a linear sequence of α-L-fucose, α-D-galactose and galacturonic acid. In this case, it preferably has a viscosity of 800–1200 mPa s (Brookfield LV31 viscosity, 12 rev/min, at 30° C.) when it is dissolved in water to a concentration of about 1% by weight.

The polyholosides according to the invention are preferably introduced into the composition in the form of an aqueous solution which may comprise from 0.1 to 5% by weight of polyholoside.

The polyholoside may be present in the final composition in an amount of from 0.01 to 5% by weight. When the polyholoside comprises a linear sequence of α-L-fucose, α-D-galactose and galacturonic acid, it is preferably present in the composition in a proportion of from 0.01 to 1% by weight.

The polyholosides according to the invention may thus be used as make-up-removing agents, in particular in a composition to clean and/or remove make-up from body or facial skin, the mucous membranes such as the lips, and/or the eyes.

The composition may be in the form of an emulsion, in particular an oil-in-water or water-in-oil emulsion, or even in the form of a multiple emulsion. It may also be in the form of an aqueous solution, which is possibly gelled, or in the form of a lotion, for example a two-phase lotion, a cream, a milk or even a foam.

The composition according to the invention may comprise an oily phase based on animal, plant, mineral, silicone, fluoro and/or synthetic oil. The oily phase may also comprise fatty alcohols or fatty acids, as well as surfactants.

Mention may be made in particular of hydrocarbon oils such as liquid paraffin or liquid petrolatum; perhydrosqualene; groundnut oil; sweet almond oil; calophyllum oil, palm oil, castor oil, avocado oil, jojoba oil, olive oil or cereal germ oil; alcohols such as oleyl alcohol, linoleyl alcohol, linolenyl alcohol, isostearyl alcohol or octyldodecanol. Mention may also be made of silicone oils such as PDMS, which are possibly phenylated, such as phenyltrimethicones.

The oily phase may also comprise a make-up-removing oil such as a fatty acid ester, in particular the esters obtained from an alcohol with a straight or branched chain having from 1 to 17 carbon atoms and from a fatty acid with a straight or branched chain having from 3 to 18 carbon atoms.

Such an ester may be selected, in particular, from dioctyl adipate, 2-ethylhexyl palmitate, diisopropyl adipate, 2-ethylhexyl hexanoate, ethyl laurate, methyl myristate, octyldodecyl octanoate, isodecyl neopentanoate, ethyl myristate, myristyl propionate, 2-ethylhexyl 2-ethylhexanoate, 2-ethylhexyl octanoate, 2-ethylhexyl caprate/caprylate, methyl palmitate, butyl myristate, isobutyl myristate, ethyl palmitate, isohexyl laurate, hexyl laurate and isopropyl isostearate.

The oily phase may be present in a proportion of 5–95% by weight in the case of an emulsion.

The composition according to the invention may additionally comprise
- an agent which allows the fatty phase to be placed in suspension, for example, a copolymer of $C_{10}$–$C_{30}$ alkyl acrylates and of acrylic or methacrylic acid or of their ester (PEMULEN TR1, PEMULEN TR2, CARBOPOL 1342 from Goodrich); or an acrylamide/methylpropanesulphonic acid copolymer (SEPPIGEL from Seppic), and/or
- an agent for dispersing the fatty phase, such as an emulsifying or vesicle system based on vesicles, which may be of nanometric size, comprising ionic or nonionic lipids, and in particular the emulsifying systems well known to those skilled in the art, comprising glyceryl stearate/PEG 100 stearate (CTFA), cetyl alcohol and stearyl alcohol.

The composition of the invention may also comprise a viscosity-modifying agent to obtain relatively gelled textures, such as:
- cellulose derivatives (carboxymethylcellulose, hydroxyethylcellulose, hydroxypropylmethylcellulose),
- natural gums such as xanthan gum, guar gum, carob gum, scleroglucans, chitin derivatives or chitosan derivatives, and carrageenans,
- polycarboxyvinyl derivatives of the Carbomer type (sold by Goodrich under the names CARBOPOL 940, 951, 980, or by 3V-Sigma under the name SYNTHALEN K or SYNTHALEN L).

The composition according to the invention may also comprise, in a known manner, adjuvants commonly used in the field considered, such as preserving agents, antioxidants, fragrances, fillers such as kaolin or starch, or even hollow microspheres, pigments, UV screening agents, sequestering agents, essential oils, dyestuffs, hydrophilic or lipophilic active agents such as moisturizers, in particular glycerol, butylene glycol, anti-inflammatory agents such as allantoin, bisabolol, anti-free-radical agents such as vitamin E or its derivatives, calmants such as cornflower water and extract of iris, depigmenting agents, biological active agents such as urea, amino acids, vitamins and derivatives thereof, proteins, salicylic acid and derivatives thereof, α-hydroxy acids, pyrrolidonecarboxylic acid and salts thereof, and ceramides. Obviously, a person skilled in the art will take care to select this or these possible additional compounds, and/or the amount thereof, such that the advantageous properties of the composition according to the invention are not, or are substantially not, adversely affected by the addition envisaged.

The composition preferably has a pH which suits the skin, generally from 5 to 8, and preferably from 5.5 to 7.5.

The composition according to the invention may be packaged in any type of packaging article. In particular, the cleaning and/or make-up-removing compositions according to the invention may advantageously be packaged in single-application (or mono-dose) packaging, namely a packaging which is such that its contents can be used entirely at a single time.

Such a packaging may be obtained in particular according to the state of the art, in particular by extrusion-blow-molding of a plastic. This process thus makes it possible for a container to be blow-molded, filled with the composition, and then sealed in a single, aseptic and continuous operation.

In a first step, the polymer, in particular in granular form, may be extruded, thereby allowing it also to be sterilized. A molding device in the form of two halves can be closed around the extruded polymer to form the body of the container. A gas such as sterile filtered air can then be injected into the mold, which will allow the container to be "blown" in the shape of the mold. The packaging thus obtained can then be filled with the cleaning composition according to the invention, the said composition preferably having been sterilized beforehand. When the required volume is filled, the packaging can be closed. Such a process is described in particular in the article "Sterility and versatility in cosmetic cream packaging" by D. Wilson, published in Cosmetics and Toiletries Manufacture Worldwide, pages 253–256, the disclosure of which is hereby incorporated by reference in its entirety.

Another subject of the invention is thus a composition to clean and/or remove make-up from the skin and/or the mucous membranes and/or the eyes, this composition comprising a heterogeneous polyholoside which comprises at least one fucose unit present in an amount of 10–90% by weight, preferably 15–35% by weight, relative to the total weight of heterogeneous polyholoside solids, where said composition is packaged in single-application form.

The invention is illustrated in greater detail in the examples which follow. The examples are intended to be illustrative and not limiting.

EXAMPLE 1

Make-up-removing milk for the face

| | |
|---|---|
| Liquid petrolatum | 7 g |
| FUCOGEL 1000, sold by Solabia | 10 g |
| (aqueous solution comprising 1% polysaccharide solids comprising fucose, galactose and galacturonic acid) | |
| Glyceryl monostearate, polyethylene glycol stearate (100 EO) | 3 g |
| Carboxyvinyl polymer | 0.4 g |
| Stearyl alcohol | 0.7 g |
| Soya proteins | 3 g |
| NaOH | 0.4 g |
| Preserving agent | qs |
| Water | qs 100 g |

This composition was made in the form of a make-up-removing milk for the face, had good cosmetic properties and was gentle and comfortable to use. The pH of the composition was about 5.5.

EXAMPLE 2

Make-up-removing lotion for the eyes

| | |
|---|---|
| FUCOGEL 1000 | 50 g |
| 2-Ethylhexyl palmitate | 10 g |
| Cyclopentadimethylsiloxane | 29 g |
| Butylene glycol | 5 g |
| Preserving agent | qs |
| Water | qs 100 g |

This lotion, which contained no surfactant, allowed effective and pleasant removal of make-up from the eyes, despite the fact that the make-up was a waterproof make-up.

EXAMPLE 3

Make-up-removing milk

| | |
|---|---|
| Octyl palmitate | 35 g |
| Glycerol | 2 g |
| FUCOGEL 1000 | 50 g |
| C10–C30 acrylates/alkylacrylates crosslinked polymer | 0.1 g |
| Triethanolamine | 0.1 g |
| Wheat amino acids | 1 g |
| Preserving agent | qs |
| Water | qs 100 g |

The milk obtained, which contained no surfactant, had good cosmetic properties.

EXAMPLE 4

Make-up-removing gel for the face

| | |
|---|---|
| Glycerol | 10 g |
| FUCOGEL 1000 | 20 g |
| Disodium cocoamphodiacetate | 1 g |
| Preserving agent | qs |
| Water | qs 100 g |

The gel obtained had good cosmetic properties.

EXAMPLE 5

Gel for cleaning with water

| | |
|---|---|
| Butylene glycol | 7 g |
| Sodium lauroyl sarcosinate | 4 g |
| FUCOGEL 1000 | 40 g |
| Triethanolamine | 0.8 g |
| Carbomer | 0.5 g |
| Preserving agent | qs |
| Water | qs 100 g |

The gel obtained had good cosmetic properties.

EXAMPLE 6

Comparative example

An oil-in-water emulsion was prepared comprising 40% by weight of an oil known to have no make-up-removing properties, liquid petrolatum. The following was added to the emulsion:

either a polyholoside according to the invention (FUCOGEL 1000)

or a gelling agent which has no make-up-removing properties (CARBOPOL 981 from Goodrich).

The make-up-removing power of the various emulsions was monitored using the so-called "make-up-removing robot" technique:

the machine was composed of a plate and an arm provided with a weight which exerted a pressure of 100 g/cm$^2$ on the plate, and which was equipped at one of its ends with a pad of cotton wool which slid over the plate.

a thin layer of a black waterproof mascara marketed under the name Kéracils by Lancôme was placed on the plate.

this plate was left to dry for 4 h.

9 unidirectional wiping motions, of a pad of cotton wool soaked with 40 drops of test composition, were then carried out, the cotton wool being changed after each wiping motion.

the amount of mascara remaining on the plate after these nine wiping motions was evaluated visually.

the number of cotton wool pads required for perfect make-up removal was noted. The total absence of mascara on the plate constituted, according to this test, perfect make-up removal.

The following results were obtained:

| | Polyholoside of the invention 0.5% AM | Control (CARBOPOL) 0.5% AM |
|---|---|---|
| Number of cotton wool pads | 4 | 5 |

AM: active material

It is thus seen that at a content of 0.5% active material, the make-up-removing power of the polyholoside according to the invention was greater than that of the control.

EXAMPLE 7

Comparative example 4 oil-in-water emulsions were prepared comprising 40% by weight of a liquid petrolatum and either a polyholoside according to the invention (FUCOGEL 1000) or a gelling agent which has no make-up-removing properties (CARBOPOL 981). These emulsions were used to remove make-up from the eyes of 20 or 24 individuals who had been madeup beforehand with Kéracils from Lancôme.

The following results were obtained.

| | Invention 0.5% AM | Control 0.5% AM | Invention 0.2% AM | Control 0.2% AM |
|---|---|---|---|---|
| rapid removal of make-up | 12/24 | 8/24 | 8/20 | 0/20 |
| normal removal of make-up | 12/24 | 12/24 | 4/20 | 8/20 |
| slow removal of make-up | 0/24 | 4/24 | 8/20 | 12/20 |
| good make-up-removing power | 24/24 | 20/24 | 12/20 | 8/20 |
| average make-up-removing power | 0/24 | 4/24 | 8/20 | 12/20 |

It is seen that the responses obtained as regards the speed of make-up-removal and the make-up-removing power of the compositions according to the invention were always greater than those of the control compositions.

Furthermore, eyelids from which make-up had been removed using the emulsions according to the invention looked and felt less greasy and less shiny than those from which make-up had been removed according to the control.

EXAMPLE 8

In this example, the make-up-removing properties of a polyholoside according to the invention were studied.

An oil-in-water emulsion was prepared comprising 40% by weight of liquid petrolatum. FUCOGEL 1000 was added and the composition obtained was tested using a make-up-removing robot.

The following results were obtained.

| Polyholoside concentration (% AM) | 0.5% | 0.4% | 0.3% | 0.2% |
|---|---|---|---|---|
| Number of cotton wool pads | 6 | 7 | 8 | 9 |

EXAMPLE 9

The make-up-removing power of an oil-in-water emulsion comprising 40% by weight of liquid petrolatum and 0.5% by weight of a make-up-removing gel composed of a mixture of FUCOGELI 1000 and CARBOPOL 981, in variable amounts, was tested. The following results were obtained:

| FUCOGEL 1000 | 0.2% | 0.25% | 0.3% | 0.4% |
|---|---|---|---|---|
| CARBOPOL 981 | 0.3% | 0.25% | 0.2% | 0.1% |
| Number of cotton wool pads | 9 | 8 | 7 | 6 |

What is claimed is:

1. A composition to clean and/or remove make-up from the skin, the mucous membranes, or the eyes, said composition comprising at least one heterogeneous polyholoside that is:

a heterogeneous polyholoside comprising at least fucose, galactose and galacturonic acid units,
   a heterogeneous alginate polyholoside, or
   a heterogeneous polyholoside substituted with at least one fatty chain and comprising at least fucose, galactose and galacturonic acid units.

2. A composition according to claim 1, wherein when said heterogeneous polyholoside is substituted with at least one fatty chain, said at least one chain contains from 8 to 30 carbon atoms.

3. A composition according to claim 1, in which said heterogeneous polyholoside comprising at least fucose, galactose and galacturonic acid units, comprises a fucose unit present in an amount of from 10 to 90% by weight relative to the weight of total heterogeneous polyholoside.

4. A composition according to claim 3, in which said fucose unit is present in an amount of from 15 to 35% by weight relative to the total weight of heterogeneous polyholoside.

5. A composition according to claim 1, in which said at least one heterogeneous polyholoside comprises a linear sequence of α-L-fucose, α-D-galactose and galacturonic acid.

6. A composition according to claim 1, in which said at least one heterogeneous polyholoside is present in the final composition in an amount of from 0.01 to 5% by weight relative to the total weight of the composition.

7. A composition according to claim 6, in which said at least one heterogeneous polyholoside is present in the final composition in an amount of from 0.01 to 1% by weight relative to the total weight of the composition.

8. A composition according to claim 1, wherein said composition is in the form of an emulsion, an aqueous solution, a lotion, a cream, a milk or a foam.

9. A composition according to claim 8, wherein said composition is in the form of an aqueous solution which is gelled.

10. A composition according to claim 8, wherein said composition is in the form of a lotion which has two phases.

11. A composition according to claim 1, wherein said composition has a pH ranging from 5 to 8.

12. A composition according to claim 11, wherein said pH ranges from 5.5 to 7.5.

13. A composition according to claim 1, wherein said composition is packaged in single-application form.

14. A method for cleaning and/or removing make-up from the skin, the mucous membranes, or the eyes, said method comprising the step of applying to the skin, mucous membranes, or eyes, a cosmetically effective amount of a composition comprising at least one heterogeneous polyholoside and a cosmetically or dermatologically acceptable support, in which said at least one heterogeneous polyholoside is:

a heterogeneous polyholoside comprising at least fucose, galactose and galacturonic acid units, a heterogeneous alginate polyholoside, or a heterogeneous polyholoside substituted with at least one fatty chain and comprising at least fucose, galactose and galacturonic acid units.

15. A method according to claim 14, wherein when said at least one heterogeneous polyholoside is substituted with at least one fatty chain, said at least one chain contains from 8 to 30 carbon atoms.

16. A method for cleaning and/or removing make-up from the skin, the mucous membranes, or the eyes, said method comprising the step of applying a cosmetically effective amount of at least one heterogeneous polyholoside to the skin, mucous membranes, or eyes in which said at least one heterogeneous polyholoside:

a heterogeneous polyholoside comprising at least fucose, galactose and galacturonic acid units, a heterogeneous alginate polyholoside, or a heterogeneous polyholoside substituted with at least one fatty chain and comprising at least fucose, galactose and cialacturonic acid units.

17. A method according to claim 14, wherein said composition is substantially non-irritating to the skin, mucous membranes, or eyes.

18. A method according to claim 14, wherein said composition has a soft feel.

19. A method according to claim 14, wherein said at least one heterogeneous polyholoside comprises a linear sequence of α-L-fucose, α-D-galactose and galacturonic acid.

20. A method according to claim 14, wherein said at least one heterogeneous polyholoside comprising at least fucose, galactose and galacturonic acid units, comprises a fucose unit present in an amount of from 10–90% by weight relative to the total weight of heterogeneous polyholoside.

21. A method according to claim 20, in which said fucose unit is present in an amount of from 15 to 35% by weight relative to the weight of total heterogeneous polyholoside.

22. A method according to claim 14, in which said at least one heterogeneous polyholoside is selected from sodium alginate, propylene glycol alginate, calcium alginate and glyceryl alginate.

23. A method according to claim 14, in which said at least one heterogeneous polyholoside is present in the final composition in an amount of from 0.01 to 5% by weight relative to the total weight of the composition.

24. A method according to claim 14, wherein said composition is in the form of an emulsion, an aqueous solution, a lotion, a cream, a milk or a foam.

25. A method according to claim 24, wherein said composition is in the form of an aqueous solution which is gelled.

26. A method according to claim 24, wherein said composition is in the form of a lotion which has two phases.

* * * * *

UNITED STATES PATENT AND TRADEMARK OFFICE
CERTIFICATE OF CORRECTION

PATENT NO. : 5,882,659
DATED : April 5, 1999
INVENTOR(S) : Marie-Laure CARREL et al.

It is certified that error appears in the above-identified patent and that said Letters Patent is hereby corrected as shown below:

IN THE CLAIMS:

Claim 16, col. 9, line 21, change "cialacturonic" to --galacturonic--.

Signed and Sealed this

Twenty-seventh Day of July, 1999

Attest:

Q. TODD DICKINSON

Attesting Officer      Acting Commissioner of Patents and Trademarks